United States Patent [19]

Pierce

[11] Patent Number: 4,607,042
[45] Date of Patent: Aug. 19, 1986

[54] METHOD FOR INCREASING PLASMA HIGH DENSITY LIPOPROTEIN (HDL)

[75] Inventor: Vanessa Pierce, Reading, England

[73] Assignee: John Wyeth & Brother Ltd., Maidenhead, England

[21] Appl. No.: 704,823

[22] Filed: Feb. 25, 1985

[30] Foreign Application Priority Data

Mar. 8, 1984 [GB] United Kingdom ............... 8406089

[51] Int. Cl.⁴ .......................................... A61K 31/445
[52] U.S. Cl. .................................................. 514/323
[58] Field of Search ....................................... 514/323

[56] References Cited

U.S. PATENT DOCUMENTS 4,428,954 1/1984 Cavalla et al. ................... 514/323

FOREIGN PATENT DOCUMENTS 1218570 1/1971 United Kingdom .

OTHER PUBLICATIONS

J. L. Archibald, "Indoramin" from *Pharmacology of Antihypertensive Drugs*, A. Scriabine, ed., (Raven Press, New York, 1980).
Weidmann et al., Hypertension, Part II, vol. 5, No. 5, Sep./Oct. 1983, pp. III-120 to III-131.
Harvard et al., J. Card. Pharmac., vol. 4, Supp. 2, pp. 5238-5241 (1982).
W. Singleton et al., Amer. Heart Journal, Nov. 1983, pp. 1265-1268.

Primary Examiner—Leonard Schenkman
Assistant Examiner—Joseph A. Lipovsky
Attorney, Agent, or Firm—Arthur G. Seifert

[57] ABSTRACT

This invention concerns the use in the treatment or prevention of atherosclerotic disorders and/or coronary heart disease of compounds of formula

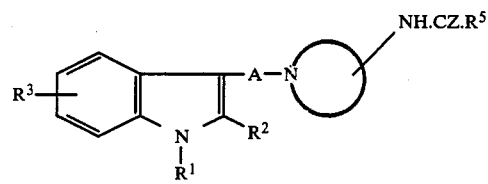

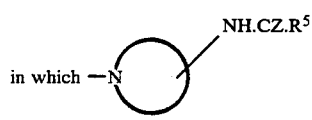

in which represents a ring system of formula

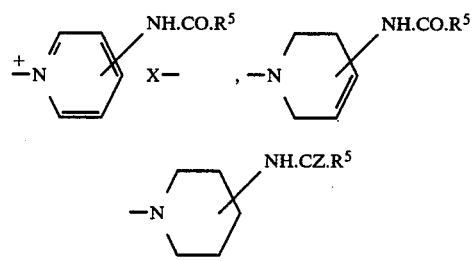

wherein $R^1$ represents hydrogen, methyl or benzyl, $R^2$ represents hydrogen or methyl, $R^3$ represents hydrogen or methoxy, $R^5$ represents phenyl, 3-indolyl, 2-furyl, diphenylmethyl, benzyloxy, or phenyl monosubstituted by chlorine, bromine, lower alkyl, carboxy, methylenedioxy, trifluoromethyl or phenyl, or represents phenyl substituted up to three times by lower alkoxy, A represents an ethylene or a 1-oxoethylene biradical, and Z is an oxo- group or, when A is ethylene and $R^5$ is phenyl, may also represent two hydrogen atoms, and X is an anion of a pharmaceutically acceptable acid.

2 Claims, No Drawings

METHOD FOR INCREASING PLASMA HIGH DENSITY LIPOPROTEIN (HDL)

This invention relates to a novel method of treatment and to the manufacture of medicaments useful in such treatment. More particularly this invention relates to a method and medicament for the treatment or prevention of atherosclerosis and/or coronary heart disease.

Epidemiological evidence gathered from studies suggests that certain physiological parameters can be used to assess the risk of developing coronary heart disease—see for example T. R. Dawber in the Framingham Heart Study: The Epidemiology of Atherosclerotic Disease. The physiological parameters of primary importance, known as risk factors, have been identified to include blood pressure and total plasma cholesterol levels. Elevation of either of these parameters above the normal range predisposes toward the development of coronary heart disease.

Although therapeutic interventions to lower blood pressure have demonstrated beneficial effects upon the incidence of stroke and congestive heart failure in hypertensive patients, it has proved difficult to demonstrate a concomitant reduction in coronary heart disease following treatment of hypertension. Indeed in some studies therapeutic intervention has been shown to increase the incidence of coronary heart disease. It is now widely believed that the reason for this finding is that current treatment regimens aggravate one or more risk factors which negates the beneficial effect of lowering blood pressure—see for example R. P. Ames, American Heart Journal, 106, 1207 (1983). One risk factor that can be affected adversely by drug therapy is the level and constituents of plasma cholesterol—see for example W. P. Castelli, American Heart Journal, 106, 1191 (1983).

It is now recognised that plasma cholesterol is carried as a lipoprotein complex of which three major fractions have been identified. These are: very low density lipoprotein (VLDL), low density lipoprotein (LDL) and high density lipoprotein (HDL). The results of the Lipid Research Clinics, Coronary Primary Prevention Trial published in Journal of the American Medical Association Vol. 251, No. 3 pps 351–374 and references cited therein demonstrate that it is very important to differentiate between the three lipoprotein fractions since they correlate differently with the incidence of coronary heart disease. Thus although elevated LDL levels appear to be associated with the development of atherosclerosis (and consequently coronary heart disease), surprisingly, the level of HDl is inversely related to the incidence of coronary heart disease with the result that elevated levels of HDL are beneficial. The importance of HDL is illustrated by Leren et al, American Heart Journal, Vol. 106, No.5, P.12, pps 1200–1206 who describe the HDL particle as a scavenger lipoprotein having the ability to take up cholesterol from the cells and transport it to the liver for excretion. These workers regard the HDL fraction as being protective whereas the VLDL and LDL fractions are atherogenic.

The Lipid Research Clinics trial (JAMA, ibid) shows that humans having plasma cholesterol levels presenting an unacceptable risk factor for coronary heart disease may reduce the risk by increasing the ratio of HDL cholesterol levels to total cholesterol levels. This ratio can be increased by elevating HDL cholesterol levels whilst reducing or not increasing the VLDL+LDL cholesterol levels.

We have now found that a class of valuable antihypertensive agents, including 3-[2-(4-benzamido-1-piperidiyl)ethyl]indole, (having the internationally approved name indoramin and claimed in UK Patent Specification No. 1218570) possesses the ability to increase plasma HDL cholesterol without increasing, and apparently decreasing, LDL and VLDL cholesterol levels thereby reducing one risk factor in coronary heart disease. Thus, indoramin can be used in the treatment of atherosclerosis.

Accordingly this invention provides a method for the treatment or prevention of atherosclerosis and/or coronary heart disease in a Primate having a plasma cholesterol lipid profile associated with or predisposed towards either of said disease states which comprises administering to said Primate a therapeutically effective amount of a compound of formula

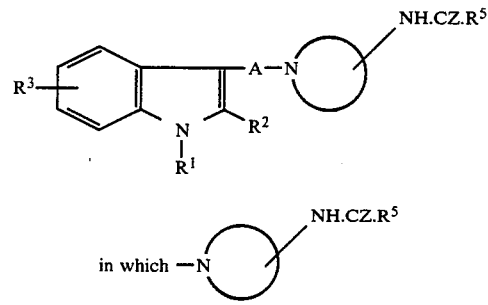

in which —N⟨ represents a ring system of formula

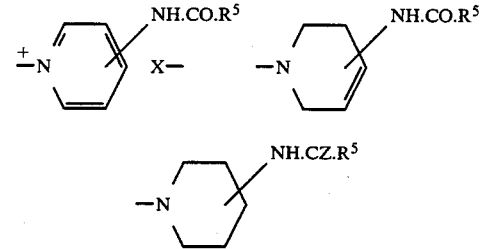

wherein $R^1$ represents hydrogen, methyl or benzyl, $R^2$ represents hydrogen or methyl, $R^3$ represents hydrogen or methoxy, $R^5$ represents phenyl, 3-indolyl, 2-furyl, diphenylmethyl, benzyloxy, or phenyl monosubstituted by chlorine, bromine, lower alkyl, carboxy, methylenedioxy, trifluoromethyl or phenyl, or represents phenyl substituted up to three times by lower alkoxy, A represents an ethylene or a 1-oxoethylene biradical, and Z is an oxo- group or, when A is ethylene and $R^5$ is phenyl, may also represent two hydrogen atoms, and X is an anion of a pharmaceutically acceptable acid.

This invention also provides use of a compound of formula I as defined above or a pharmaceutically acceptable salt thereof in the preparation of a medicament for the treatment or prevention of atherosclerosis or coronary disease.

Examination of serum VLDL, LDL, and HDL levels of commonly available laboratory species revealed that the patas monkey possesses a profile resembling that of man. The representative compound of formula I, indoramin, was therefore investigated for its effect on lipoproteins in monkeys fed a high cholesterol diet. In man it is common to consider total plasma cholesterol concentration above 7 mmol/l as hypercholesterolemic. In order to make the animal model approximate the expected disease state in man the plasma cholesterol concentration of the monkeys was raised from 2.52±0.11 to 9.39±1.7 mmol/l by feeding them a high cholesterol diet. The test procedure used was as follows:

Six female patas monkeys were fed a commercially prepared pelleted diet (CRM, Labsure) and orally dosed with lactose containing capsules twice daily (9 am and 5 pm). Throughout the study blood samples (5 ml) were taken from the femoral vein at weekly intervals following an overnight fast.

After a three week "run in" period (time $T_o$) the diet was changed to a high cholesterol mixture [skimmed milk powder, 30%; tallow, 15%; Nutramol 30, 17.5% (supplied by SDS Ltd. Stepfield, Witham, Essex, CN8 3AD); casein, 13%; ground whole wheat, 19.8%; essential vitamins and minerals, 4.2%; cholesterol, 0.5%]. After a further three weeks (time $T_1$) the monkeys were divided into two groups of three. The animals in one of these groups continued to receive the placebo and the second group was dosed with indoramin, monohydrochloride (2.5 mg/Kg p.o. twice daily). After eight weeks (time $T_2$) of the regimen the treatments were crossed over. Thus after the eleventh week on the modified diet monkeys previously receiving indoramin were given lactose and vice versa.

Analysis of Blood Samples

The blood samples were collected into lithium-heparin tubes and then centrifuged at 3000 g for 10 minutes. The plasma was then decanted and frozen until the lipid analysis was performed. When thawed the samples were defibrinated and divided into two fractions.

The lipoprotein fractions were separated by electrophoresis on cellulose acetate membranes in Tris-buffer (pH 8.8) at 180 V for 25 minutes). The cholesterol content of each fraction was visualized with a chromogen using the CHOD-PAP method (Helena HDL Kit super ZX 5471 sold by Helena Laboratories, 1530 Lindbergh Drive, Beaumont, Tex., USA) of Allain et al, 1974 Clinical Chemistry 20: 470–475. Quantification of the cholesterol content the HDL and VLDL+LDL (i.e. [HDL(C), VLDL(C)+LDL(C)] fraction was by densitometry at 505 nm (Gelman ACD18 Densitometer). A second sample of plasma was taken to measure the total cholesterol content of each sample using the CHOD-PAP method with a Boehringer Kit (BCL cholesterol C-system no. 290319)

Results are shown in Tables 1 and 2.

TABLE 1

| High density lipoprotein cholesterol concentrations (mmol/L) in the monkey | | | | | | |
|---|---|---|---|---|---|---|
| | Monkey 1 | Monkey 2 | Monkey 3 | Monkey 4 | Monkey 5 | Monkey 6 |
| TIME IN WEEKS | PLACEBO | | | PLACEBO | | |
| 0 ($T_o$) | 1.03 | 0.89 | 0.66 | 1.19 | 0.98 | 1.01 |
| 1 | 2.51 | 1.72 | 2.62 | 2.97 | 1.72 | 2.24 |
| 2 | 3.16 | 1.71 | 2.84 | 2.96 | 2.17 | 2.14 |
| 3 ($T_1$) | 3.79 | 1.93 | 3.39 | 3.53 | 2.56 | 2.37 |
| | PLACEBO | | | INDORAMIN (2.5 mg/kg p.o. twice daily) | | |
| 1 | 3.67 | 1.82 | 4.62 | 4.72 | 2.40 | 2.40 |
| 2 | 3.73 | 1.42 | 4.07 | 5.11 | 2.49 | 3.27 |
| 3 | 6.37 | 1.21 | 5.19 | 5.12 | 2.69 | 3.93 |
| 4 | 6.15 | 2.08 | 4.93 | 5.36 | 2.77 | 3.48 |
| 5 | 3.62 | 1.85 | 2.1 | 3.61 | 2.60 | 3.31 |
| 6 | 4.06 | 1.96 | 3.14 | 3.14 | 1.54 | 2.93 |
| 7 | 3.53 | 1.48 | 2.65 | 4.01 | 2.25 | 4.09 |
| 8 ($T_2$) | 3.41 | 1.61 | 2.62 | 4.29 | 2.60 | 3.47 |
| MEAN CHANGES FROM $T_1$ | −0.49 ± 0.14 (−16%) | | | +0.63 ± 0.31* (+23%) | | |
| | INDORAMIN (2.5 mg/kg p.o. twice daily) | | | PLACEBO | | |
| 1 | 4.07 | 1.79 | 2.69 | 3.86 | 2.83 | 3.86 |
| 2 | 4.10 | 2.27 | 2.54 | 3.45 | 2.34 | 2.83 |
| 3 | 3.70 | 2.12 | 2.17 | 2.61 | 2.00 | 3.16 |
| 4 | 4.24 | 1.89 | 3.18 | 3.26 | 1.95 | 2.56 |
| 5 | 4.24 | 1.92 | 3.64 | 3.35 | 1.90 | 2.70 |
| MEAN CHANGES FROM $T_2$ | +0.72 ± 0.21* (+27%) | | | −0.80 ± 0.07 (−24%) | | |

*significantly different from contemporaneous placebo group

TABLE 2

| Low density + Very low density lipoprotein cholesterol concentrations (mmol/L) in the monkey | | | | | | |
|---|---|---|---|---|---|---|
| | Monkey 1 | Monkey 2 | Monkey 3 | Monkey 4 | Monkey 5 | Monkey 6 |
| TIME IN WEEKS | PLACEBO | | | PLACEBO | | |
| 0 ($T_o$) | 1.30 | 1.58 | 1.97 | 1.77 | 1.58 | 1.17 |
| 1 | 3.10 | 2.13 | 4.79 | 4.42 | 2.11 | 2.6 |
| 2 | 6.81 | 2.94 | 9.43 | 7.49 | 3.28 | 3.98 |
| 3 ($T_1$) | 7.60 | 2.84 | 11.28 | 9.32 | 3.98 | 3.74 |
| | PLACEBO | | | INDORAMIN (2.5 mg/kg p.o. twice daily) | | |
| 1 | 6.18 | 2.59 | 11.81 | 9.47 | 2.96 | 3.02 |
| 2 | 5.11 | 1.99 | 13.06 | 9.24 | 2.10 | 2.49 |
| 3 | 6.69 | 1.37 | 10.90 | 9.37 | 2.33 | 2.26 |

TABLE 2-continued

| Low density + Very low density lipoprotein cholesterol concentrations (mmol/L) in the monkey | | | | | | |
|---|---|---|---|---|---|---|
| | Monkey 1 | Monkey 2 | Monkey 3 | Monkey 4 | Monkey 5 | Monkey 6 |
| 4 | 8.45 | 1.76 | 12.03 | 7.0 | 2.47 | 3.32 |
| 5 | 7.7 | 2.24 | 13.6 | 9.18 | 2.83 | 3.34 |
| 6 | 6.38 | 2.38 | 12.64 | 8.9 | 2.46 | 2.86 |
| 7 | 8.27 | 2.43 | 12.2 | 9.07 | 2.74 | 3.14 |
| 8 ($T_2$) | 6.85 | 2.57 | 11.16 | 8.10 | 2.75 | 2.88 |
| MEAN CHANGES FROM $T_1$ | | $-0.38 \pm 0.19$ (−7%) | | | $-1.1 \pm 0.2$* (−22%) | |
| | | INDORAMIN (2.5 mg/kg p.o. twice daily) | | | PLACEBO | |
| 1 | 8.94 | 3.26 | 14.08 | 11.26 | 3.36 | 3.04 |
| 2 | 8.22 | 2.59 | 14.88 | 13.17 | 4.11 | 4.05 |
| 3 | 8.04 | 3.82 | 9.43 | 9.56 | 3.87 | 3.46 |
| 4 | 7.84 | 2.57 | 11.87 | 9.13 | 2.42 | 2.48 |
| 5 | 7.84 | 2.08 | 9.44 | 7.88 | 2.31 | 2.27 |
| MEAN CHANGES FROM $T_2$ | | $-0.4 \pm 0.78$ (−7%) | | | $0.42 \pm 0.11$ (−13%) | |

*significantly different from contemporaneous placebo group.

In detail Table 1 shows that at the end of the eight week period ($T_2$) following the predose period (three weeks) the high density lipoprotein cholesterol concentrations increased significantly in the three monkeys receiving indoramin (2.5 mg/kg twice daily) relative to the three monkeys receiving placebo. The difference represents a 39% increase compared to placebo. After only five further weeks following crossover the three monkeys now receiving the indoramin in the same dosage as previous group showed a significant increase relative to the group receiving placebo. These results demonstrate incoramin's marked ability to alter favourably HDL cholesterol concentrations and indicate a use in the treatment of diseases such as atherosclerosis.

The results in Table 2 of the VLDL(C)+LDL(C) concentrations show that after the eight week period following $T_1$ the three monkeys receiving indoramin (2.5 mg/kg p.o. twice daily) showed a significantly lower level of VLDL(C)+LDL(C) than the placebo-receiving monkeys. This result taken alone shows that indoramin appears to have a beneficial effect in lowering the LDL(C) and VLDL(C) levels. However, after the crossover period no statistically significant change from placebo was noted after five weeks and a longer period is required to show the effect.

These results show indoramin's ability not to increase and apparently to decrease VLDL(C)+LDL(C) levels.

The results from Tables 1 and 2 have been used to calculate the 'cholesterol ratio' (i.e. HDL(C)/[VLDL(C)+LDL(C)] at the same time points for each of the six monkeys and the values obtained are shown in Table 3. The cholesterol ratio is regarded as an alternative way of presenting the data to show the beneficial effect of indoramin on the lipoprotein cholesterol levels. The ability of indoramin to increase the cholesterol ratio before and after crossover is shown by the results in Table 3.

TABLE 3

| | Cholesterol ratio in monkeys | | | | | |
|---|---|---|---|---|---|---|
| | Monkey 1 | Monkey 2 | Monkey 3 | Monkey 4 | Monkey 5 | Monkey 6 |
| TIME IN WEEKS | | PLACEBO | | | PLACEBO | |
| 0 ($T_o$) | 0.79 | 0.56 | 0.34 | 0.67 | 0.62 | 0.86 |
| 1 | 0.81 | 0.81 | 0.55 | 0.67 | 0.82 | 0.86 |
| 2 | 0.46 | 0.58 | 0.30 | 0.40 | 0.66 | 0.54 |
| 3 ($T_1$) | 0.50 | 0.68 | 0.30 | 0.34 | 0.64 | 0.63 |
| | | PLACEBO | | | INDORAMIN | |
| 1 | 0.59 | 0.70 | 0.39 | 0.5 | 0.62 | 0.79 |
| 2 | 0.73 | 0.71 | 0.31 | 0.55 | 1.19 | 1.31 |
| 3 | 0.95 | 0.88 | 0.48 | 0.55 | 1.15 | 1.74 |
| 4 | 0.72 | 1.18 | 0.41 | 0.77 | 1.12 | 1.05 |
| 5 | 0.47 | 0.83 | 0.15 | 0.39 | 0.92 | 0.99 |
| 6 | 0.64 | 0.82 | 0.24 | 0.35 | 0.63 | 1.02 |
| 7 | 0.43 | 0.61 | 0.22 | 0.44 | 0.82 | 1.30 |
| 8 ($T_2$) | 0.5 | 0.63 | 0.23 | 0.53 | 0.95 | 1.20 |
| MEAN CHANGE FROM $T_1$ | | $-0.04 \pm 0.02$ | | | $+0.36 \pm 0.11$* | |
| | | INDORAMIN | | | PLACEBO | |
| 1 | 0.46 | 0.55 | 0.19 | 0.34 | 0.84 | 1.27 |
| 2 | 0.5 | 0.88 | 0.17 | 0.26 | 0.57 | 0.7 |
| 3 | 0.46 | 0.55 | 0.23 | 0.27 | 0.52 | 0.91 |
| 4 | 0.54 | 0.74 | 0.26 | 0.36 | 0.81 | 1.03 |
| 5 | 0.54 | 0.92 | 0.39 | 0.43 | 0.82 | 1.20 |
| MEAN CHANGE FROM $T_2$ | | $+0.13 \pm 0.06$* | | | $-0.08 \pm 0.04$ | |

*significantly different from contemporaneous placebo group

When used in the method of this invention a compound of formula I or a pharmaceutically acceptable acid addition or quaternary ammonium salt thereof may be administered alone or in the form of a pharmaceutically acceptable composition. Suitable carriers are well known in the art. The particular dosage will depend on the chosen route of administration and standard pharmaceutical practice. Preferably the composition is in unit dosage form, e.g. tablets or capsules. Based on the effective dose found in monkeys the expected dosage in humans for indoramin as a promoter of HDL(C) is from about 10 mg to about 75 mg per day, preferably 25 to 50 mg per day, e.g. in two or more doses. Should the person being treated also require antihypertensive therapy then the dosage may be increased, e.g. up to 200 mg/day to also bring blood pressure under control.

In a further aspect, this invention provides a method for increasing plasma high density lipoprotein cholesterol concentration in a Primate having a cholesterol lipid profile associated with or predisposed toward said disease state which comprises administering a therapeutically effective amount of a compound of formula I as defined above or a pharmaceutically acceptable salt thereof.

The term lower as used herein to qualify a group means that the group contains 1 to 6 carbon atoms, preferably 1 to 4.

I claim:

1. A method for increasing plasma high density lipoprotein (HDL) cholesterol concentration in a primate, including Man, having a plasma lipid cholesterol level associated with or predisposed towards the development of atherosclerosis or coronary heart disease, which comprises administering to said primate a therapeutically effective amount of the compound 3-[2-(4-benzamido-1-piperidyl)ethyl]indole or a pharmaceutically acceptable salt thereof.

2. A method for increasing the plasma cholesterol ratio (HDL(C)/[VLDL(C)+LDL(C)]) in a primate, including man, having a plasma lipid cholesterol level associated with or predisposed towards the development of atherosclerosis or coronary heart disease, which comprises administering to said primate a therapeutically effective amount of the compound 3-[2-(4-benzamido-1-piperidyl)-ethyl]indole or a pharmaceutically acceptable salt thereof.

* * * * *